United States Patent
Kleiman et al.

(10) Patent No.: US 6,417,673 B1
(45) Date of Patent: Jul. 9, 2002

(54) SCANNING DEPLETION MICROSCOPY FOR CARRIER PROFILING

(75) Inventors: Rafael Nathan Kleiman, New York, NY (US); Megan Lorraine O'Malley, Neshanic Station; Gregory L. Timp, Pittstown, both of NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/196,489

(22) Filed: Nov. 19, 1998

(51) Int. Cl.[7] .................. H01H 31/02; G01R 31/02; G01N 23/00
(52) U.S. Cl. .................. 324/537; 324/754; 250/306
(58) Field of Search .................. 324/537, 751, 324/752, 754, 763, 756; 250/306, 307; 73/105

(56) References Cited

U.S. PATENT DOCUMENTS

| | | | |
|---|---|---|---|
| 4,943,719 A | * 7/1990 | Akamine et al. | 250/306 |
| 5,021,364 A | * 6/1991 | Akamine et al. | 250/306 |
| 5,051,379 A | * 9/1991 | Bayer et al. | 250/306 |
| 5,065,103 A | * 11/1991 | Slinkman et al. | 324/662 |
| 5,066,358 A | * 11/1991 | Quate et al. | 250/306 |
| 5,217,907 A | * 6/1993 | Bulucea et al. | 324/715 |
| 5,267,471 A | * 12/1993 | Abraham et al. | 250/306 |
| 5,319,977 A | * 6/1994 | Quate et al. | 324/662 |
| 5,488,305 A | * 1/1996 | Bloom et al. | 324/537 |
| 5,523,700 A | * 6/1996 | Williams et al. | 324/765 |
| 5,581,083 A | * 12/1996 | Majumdar et al. | 250/306 |
| 5,652,445 A | * 7/1997 | Johnson | 324/252 |
| 5,723,981 A | * 3/1998 | Hellemans et al. | 324/756 |
| 5,781,017 A | * 7/1998 | Cole, Jr. et al. | 324/751 |
| 6,005,400 A | * 12/1999 | Thundat et al. | 324/752 |
| 6,091,248 A | * 7/2000 | Hellemans et al. | 324/756 |
| 6,094,971 A | * 8/2000 | Edwards et al. | 73/105 |
| 6,198,300 B1 | * 3/2001 | Doezema et al. | 324/754 |

OTHER PUBLICATIONS

"Junction Delineation . . . Microscopy" by R.N. Kleiman et al, IEDM Technical Digest, pp. 691–694, 1997.
"Direct Channel . . . Microscopy" by R.N. Kleiman et al, Symposium on VLSI Technology Digest, pp. 138–139, Jun. 1998.

* cited by examiner

*Primary Examiner*—Michael Sherry
*Assistant Examiner*—Jermele M. Hollington
(74) *Attorney, Agent, or Firm*—Lowenstein Sandler, PC

(57) ABSTRACT

In an imaging system for carrier profiling of a device structure, a doped semiconductor tip is utilized as an active dynamic sensing element for successively probing spaced-apart portions of the structure. At each probe position, the bias voltage applied between the tip and the structure is varied. While the bias voltage is being varied, a measurement is taken of the change in capacitance that occurs between the tip and the structure. These measurements provide an accurate high-resolution high-contrast image that is representative of the carrier profile of the probed portions of the device structure.

16 Claims, 3 Drawing Sheets

SCANNING DEPLETION MICROSCOPY FOR CARRIER PROFILING

BACKGROUND OF THE INVENTION

This invention relates to the characterization of structures and, more particularly, to an imaging system for obtaining carrier profiles of regions in a semiconductor device.

In an article entitled "Junction Delineation of 0.15 $\mu$m MOS Devices Using Scanning Capacitance Microscopy" by R. N. Kleiman, M. L. O'Malley, F. H. Bauman, J. P. Gamo and G. L. Timp, *IEDM Technical Digest*, pages 691–694, 1997, scanning capacitance microscopy (SCM) is described as a technique for characterizing the cross-sectional doping profile of semiconductor structures such as metal-oxide-semiconductor (MOS) transistor devices. Such characterization provides important information for device development and for optimizing the process sequence utilized to make the devices.

Conventional SCM imaging involves positioning a probe tip at successive spaced-apart locations on the surface of a sample. At each position, a measurement is made of the change in capacitance that occurs as the bias voltage applied between the tip and sample is varied. By plotting this quantity (dC/dV) as a function of probe position, it is possible to obtain an indication of the doping profile in the sample, as is well known.

Heretofore, SCM imaging of semiconductor samples has been carried out using small-diameter metal-coated probe tips such as cobalt-silicide-coated tips. In practice, metal-coated tips having a diameter as small as about 30-to50 nanometers (nm) have been employed. By utilizing such small-diameter tips, it is possible to resolve channels of devices with gate lengths as small as approximately 150 nm in MOS devices.

Unfortunately, however, the results typically obtained in SCM imaging with metal-coated tips depend strongly on the value of the bias voltage applied between the tip and the sample. In particular, due to the interaction of the metal-coated tip with the sample, specifically in the built-in depletion region associated with the p-n junctons in the sample, the locations of the junctions move as the applied bias voltage is varied. This considerably complicates the interpretation of the doping information obtained during scanning. Moreover, the resolution and contrast obtainable with metal-coated tips are often less than that required for characterizing ultra-small devices.

Accordingly, continuing efforts have been directed by workers skilled in the art aimed at trying to improve SCM-type imaging of semiconductor devices. In particular, these efforts have been focussed on attempting to improve the resolution and contrast of the SCM images and, further, on attempting to locate the p-n junctions in the device in a simple and accurate manner. It was recognized that these efforts, if successful, could significantly enhance the value of SCM-type imaging as an important tool for characterizing the carrier profile of semiconductor devices.

SUMMARY OF THE INVENTION

In accordance with the principles of the present invention, a probe tip made of a material that is capable of exhibiting depletion effects is utilized as an active dynamic element for SCM-type imaging of a sample. The concentration of carriers in the tip is selected to be on the order of or less than the highest concentration of carriers in any sample portion to be probed.

In one particular illustrative embodiment of the present invention, an ultra-small probe tip made of a doped semiconductor material is utilized as an active dynamic element for SCM-type imaging of a semiconductor device. By controlling the doping and bias voltage of the probe tip relative to the device, an accurate high-resolution high-contrast carrier profile of the device is obtained. Importantly, the inventive technique is capable of imaging both semiconducting and non-semiconducting (insulating and metallic) regions of a device structure. These unique capabilities of the invention stem from carrier depletion effects that are selectively controlled to occur in the doped probe tip.

In one specific illustrative embodiment of the invention, a positively-biased n-doped silicon probe tip is step-wise scanned over the cross-section of an n-p-n MOS device while the bias voltage applied between the probe tip and the device is varied. At each step of the scan, a value of dC/dV is measured. These measurements are representative of the cross-sectional carrier profile of the device.

In another specific embodiment of the invention, a negatively-biased p-doped silicon probe tip is step-wise scanned in a similar fashion over the cross-section of a p-n-p MOS device to obtain a representation of the carrier profile of the device.

BRIEF DESCRIPTION OF THE DRAWING

A complete understanding of the present invention and of the above and other features and advantages thereof may be gained from a consideration of the following detailed description presented hereinbelow in connection with the accompanying drawing, not drawn to scale, in which.

DETAILED DESCRIPTION

Figure 1:
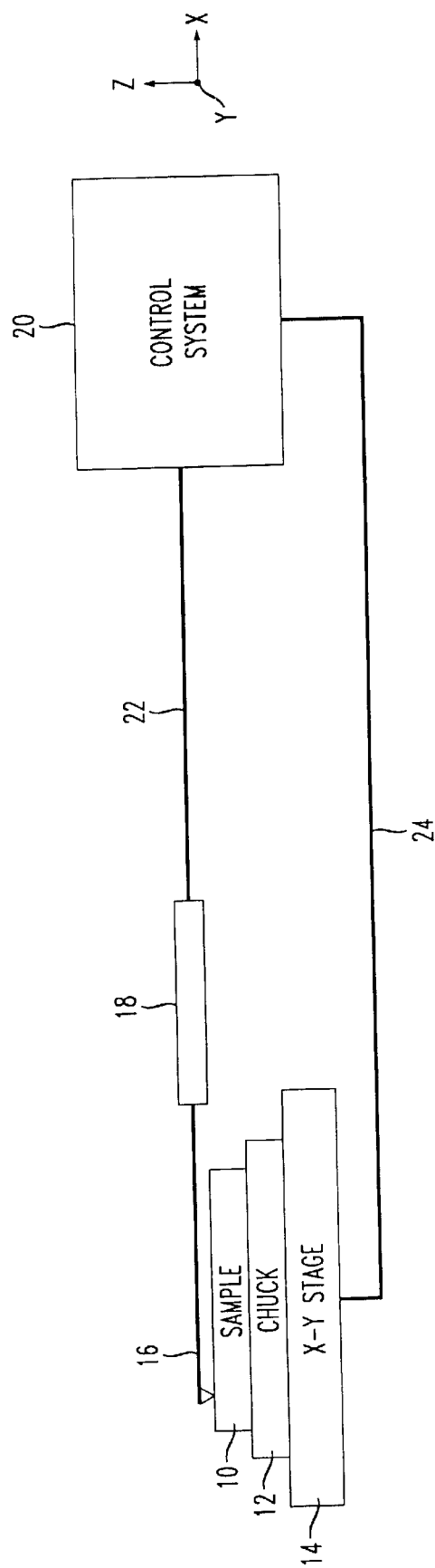
FIG. 1 is a simplified schematic showing of conventional apparatus designed to carry out SCM imaging.

A conventional SCM imaging system is schematically represented in simplified form in FIG. 1. As shown, a sample 10 to be probed is mounted on a chuck 12 that is supported by a standard X-Y stage 14. Further, a probe 16 mechanically supported by an electrically conductive holder 18 is shown in contact with the top surface of the sample 10. In response to electrical signals applied to the X-Y stage 14 from a control system 20, the stage 14 is successively moved to pre-specified positions. In that way, specified small-area portions of the sample 10 are successively moved under the probe 16 for imaging purposes.

At each specified X-Y position, a variable bias voltage comprising an alternating-current (a-c) signal superimposed on a direct-current (d-c) voltage is applied across the sample 10 of FIG. 1. This variable bias voltage is supplied by the control system 20 and applied to the sample 10 via electrical leads 22 and 24, the X-Y stage 14, the chuck 12, the holder 18 and the probe 16.

At each specified X-Y position, a variable bias voltage is applied to the sample 10 of FIG. 1 while the resulting change in capacitance across the sample attributable to the change in bias voltage is measured by the system, in a manner well known in the art. By plotting these measurements (dC/dV) as a function of probe position, significant information about the sample can be obtained. Thus, for example, the depicted SCM apparatus can be utilized to obtain a two-dimensional profile of the doping in the n- and p-regions of a semiconductor device.

In a standard SCM apparatus of the type depicted in FIG. 1, the probe 16 includes a metal-coated tip. A conventional probe comprises, for example, a cobalt-silicide-coated tip. For purposes of high resolution, the diameter of the metal-coated tip is typically made as small as possible. In practice, metal-coated tips having tip diameters as small as about 30-to-50 nm have been achieved. Such metal-coated tips are capable of resolving MOS device features such as channels resulting from devices with gate lengths as small as approximately 150 nm. But this gate length (150 nm) considerably exceeds that of some recently described MOS devices. Accordingly, available metal-coated tips lack sufficient resolution to successfully image the features of such small devices.

Moreover, SCM images produced in a conventional apparatus of the type represented in FIG. 1, utilizing metal-coated probe tips, show a strong dependence on the value of the applied bias voltage. In practice, the interpretation of the doping information of the sample is not straightforward. This is so because the locations of the p-n junctions in the sample are found to move with variations in the applied bias voltage. This effect has been shown to be due to the interaction of the metal-coated tip with the sample, specifically in the built-in depletion regions associated with the junctions.

Figure 2:
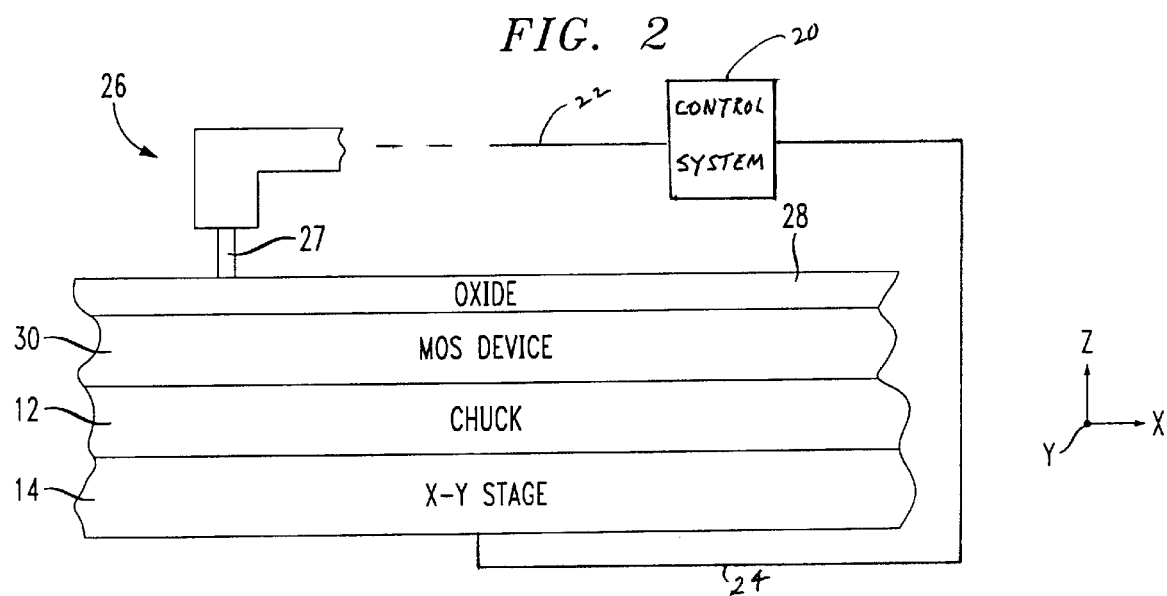
FIG. 2 depicts a portion of the FIG. 1 apparatus modified to include a specific illustrative probe tip made in accordance with the principles of the present invention.

In accordance with one specific illustrative embodiment of the principles of the present invention, the probe tip of an SCM apparatus of the type represented in FIG. 1 is made of a doped semiconductor material. Illustratively, such a probe, designated by reference numeral 26 in FIG. 2, is shaped by conventional semiconductor processing techniques from a standard piece of doped silicon to form an element terminating in a tip 27. More specifically, the probe 26 achieved thereby includes an ultra-small tip 27 designed to contact the surface of a sample to be probed. By way of a particular illustrative example, the contacting tip 27 of the depicted probe 26 has a rectangular cross-section in the indicated X-Y plane of about ten nm by ten nm. Illustratively, the Z-direction height of the tip 27 is approximately 100 nm. Further, the contacting or lower-end portion of the tip 27 is rounded with, for example, a radius of curvature of about five nm. In FIG. 2, the ultra-small tip 27 of the probe 26 is shown as being in contact with the top surface of a sample comprising an oxide layer 28 overlying an MOS device 30.

Ultra-small probe tips made by standard semiconductor processing techniques result in an immediate improvement in the resolution of images obtained with an SCM apparatus. But, as will be described in detail later below, the fact that these small tips are, in accordance with one specific illustrative embodiment of the invention, made of a doped semiconductor material result in better resolution than if comparably-sized metal-coated probe tips were utilized. Thus, for example, employing the herein-considered inventive SCM-type technique, MOS devices having gate lengths as small as 60 nm can be successfully imaged with ten-nm-diameter doped semiconductor tips.

Significant advantages other than better resolution accrue to the use of ultra-small doped semiconductor tips to perform SCM-type imaging. These other advantages include better-contrast images and images that more accurately locate the p-n junctions in MOS devices, as will be described in detail below.

For purposes of a specific illustrative example, imaging of a portion of an n-p-n MOS device will be described. In particular, a slice of the device structure shown in FIG. 3 will be imaged.

Figure 3:
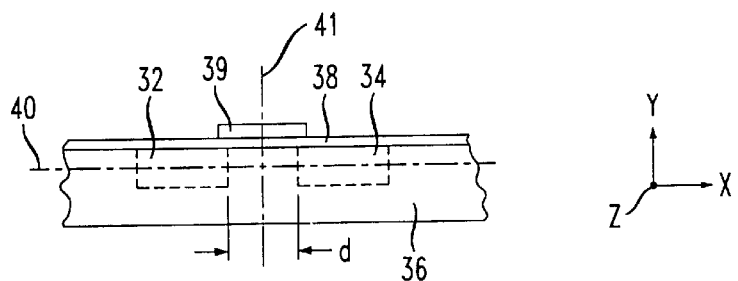
FIG. 3 represents in cross-section a portion of an MOS device of the type to be imaged by the inventive apparatus.

FIG. 3 shows a portion of a conventional MOS device. By way of example, the device includes spaced-apart source and drain regions 32 and 34 formed in a p-type silicon substrate 36. The depicted device also includes a standard gate-oxide layer 38 and a gate electrode 39 (which may comprise, for example, layers of a doped semiconductor and a metal). The spacing d between the regions 32 and 34 constitutes the so-called channel length of the device.

In state-of-the-art devices, gate lengths are being scaled down to 100 nm and below. For such small devices, especially where process flows are not yet established, it is extremely valuable to be able to image the two-dimensional carrier profile of the device cross-section. In that way, the position of the p-n junctions in the device can be located and the length of the channel in an actual device can be determined. Such imaging can provide important feedback information for optimizing the process flow and for providing modeling tools for use in device development.

Illustratively, to prepare the FIG. 3 device for SCM-type imaging, a slice thereof is obtained by cutting through an actual device in parallel spaced-apart X-Y planes. For example, a sample about 0.5 millimeters thick is thereby obtained. Dot-dash reference line 40 in FIG. 3 denotes approximately the direction in which scanning will occur overlying one X-Y face of the sample slice.

Additionally, in accordance with the invention, it is feasible also to provide SCM-type images of metallic and insulating regions of a semiconductor device. In particular, it is possible, utilizing a doped semiconductor probe tip, to provide respectively different contrasting images while probing metallic and insulating regions. Such contrasting images are not possible with a metal tip in a conventional SCM system.

Hence, in accordance with the invention, it is feasible both to image the differently doped n- and p-regions of the n-p-n device shown in FIG. 3 and to image metallic and insulating portions thereof Thus, for example, by scanning a doped semiconductor probe tip in the Y direction approximately along the dot-dash reference line 41 shown in FIG. 3, it is possible to provide respectively contrasting images (based on different dC/dV values) as the probe tip moves from a point overlying the channel in the p region 36, to a point overlying the gate oxide 38, to a point overlying the doped semiconductor layer of the gate 39, and finally to a point overlying the metal layer of the gate 39.

Illustratively, emphasis herein-below will be directed to scanning the FIG. 3 structure in the direction indicated by the reference line 40. In that case, contrasting SCM-type images between differently doped semiconductor regions are provided. Following that description, it will be apparent that the inventive technique is also capable of providing SCM-type contrasting images between metals and insulators.

Figure 4:
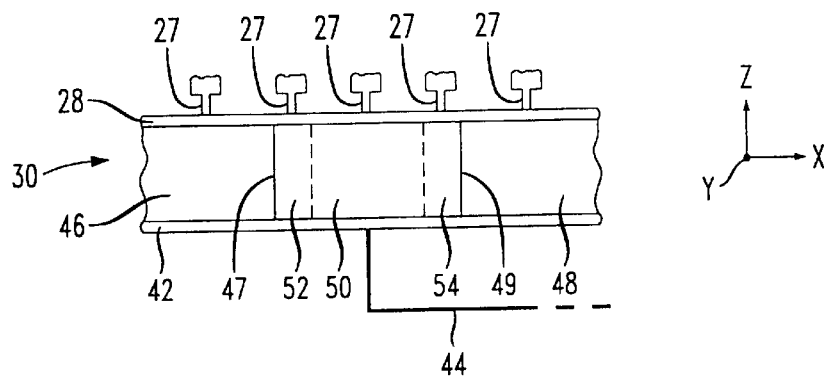
FIG. 4 shows a cross-sectional sample of the FIG. 3 device, with various probe tip positions indicated thereon.

A cross-sectional view of the aforespecified sample slice, taken in a plane parallel to the indicated X-Z plane, is represented in FIG. 4. As shown, the semiconductor portion of the sample, which corresponds to the device 30 depicted in FIG. 2, also includes a dielectric layer 28 and a conductive layer 42. The layer 28 corresponds to the oxide layer 28 shown in FIG. 1 The layer 28 is, for example, a naturally occurring layer of silicon dioxide that forms in air on exposed silicon surfaces. Or the layer 28 can be purposely formed in standard ways on the indicated silicon surface. The layer 28 has, for example, a Z-direction thickness of about 1-to-2 nm. And the conductive layer 42 comprises, for example, a 100-nm-thick layer of metal.

Electrical connections are respectively made to the layers 28 and 42 of the sample shown in FIG. 4. In turn, these connections extend to the control system 20 of FIG. 1. Lead 44 in FIG. 4 represents in effect the electrical connection that is made in FIG. 1 to the sample 10 via the chuck 12, the X-Y stage 14 and the lead 24. Further, some of the successive X-direction positions that the probe tip 27 of FIG. 2 assumes as it scans over the surface of the depicted sample are schematically indicated in FIG. 4. At each such position, an electrical connection extends to the control system 20 (FIG. 1) via the probe tip 27 and the probe holder 18 and the lead 22 of FIG. 1.

In a standard SCM system, a d-c bias voltage is applied between the probe tip 16 (FIG. 1) and the sample 10. This establishes a carrier depletion depth in the sample. Further, an a-c voltage is superimposed on the d-c bias. This modulates the depletion depth in the sample, which may be modeled as a moving capacitor plate. In that way, the capacitance across the sample varies with changes in the applied bias voltage. Thus, the measured signal is proportional to the quantity dC/dV. The sign of this quantity depends on the carrier type (n- or p-type) in the sample, and the magnitude of dC/dV is inversely proportional to the carrier concentration, as is well known.

In accordance with the present invention, depletion effects that occur in a biased probe tip made of a doped semiconductor material are utilized to advantage in an SCM-type system. By appropriate selection of the bias voltage and of the doping of such a tip, an active dynamic tip characterized by advantageous depletion effects is provided. By utilizing such a tip as an active sensor, high-resolution high-contrast images of p- and n-regions (as well as of metal and insulating regions) in a device structure are obtained. Moreover, depletion effects in the doped tip enable elimination of some of the bias-dependent effects seen in standard SCM systems that include metal-coated probe tips.

To illustrate the principles of the present invention, SCM-type imaging (or, more descriptively, scanning-depletion-microscopy imaging) of a simple n-p-n MOS device sample will be specified below. Such a sample is depicted in FIG. 4, where n-regions 46 and 48 constitute the source and drain regions of the device. Further, the p-type channel region of the device is designated by reference numeral 50. Nominal boundaries 47 and 49 are respectively indicated between the channel 50 and the source and drain regions 46 and 48. So-called depletion regions 52 and 54 actually respectively exist between the channel region 50 and the source and drain regions 46 and 48. The p-n junctions between the p-region 50 and the respective n-regions 46 and 48 are located in the depletion regions 52 and 54. In the particular example considered herein, the p-n junction between the n-region 46 and the p-region 50 exists close to the indicated boundary 47, and the p-n junction between the n-region 48 and the p-region 50 exists close to the indicated boundary 49. This is so because the doping level in the source/drain regions is much higher than that in the channel.

In one particular example of the principles of the present invention, the n-regions 46 and 48 shown in FIG. 4 are each assumed to be doped to a concentration of about $2\times10^{19}$ dopants per cubic centimeter ($cm^{-3}$) with, for example, arsenic, and the p-region 50 is assumed to be doped to a concentration of approximately $5\times10^{17}$ $cm^{-3}$ with, for example, boron.

In accordance with the invention, the tip 27 of the semiconductor probe 26 is doped with the same impurity type as is used to dope the most highly doped regions of the MOS device to be scanned. Thus, for the particular example shown in FIG. 4 and specified above, the tip 27 comprises an n-doped member. Moreover, the concentration of dopants in the tip 27 is selected to be approximately on the order of or, advantageously, less than the concentration of dopants in the n-doped source and drain regions 46 and 48. Additionally, the polarity of the bias voltage applied to the probe tip 27 is such as to tend to deplete the tip. Thus, for an n-doped tip 27, a variable positive bias voltage is applied thereto. As the bias voltage goes more positive, carriers (electrons) are moved upwards in the tip 27 (in the Z direction in FIG. 2) away from the oxide layer 28. This effect causes the overall measured capacitance of the structure to decrease. On the other hand, when the bias voltage goes less positive, carriers are moved downwards in the tip 27, thereby causing the overall measured capacitance to increase. The measured dC/dV is thus negative. In this arrangement, as will be clear from the description below, such effects in the tip 27 significantly enhance the imaging process.

In a specific illustrative embodiment of the present invention, where it is desired to obtain an SCM-type image of an n-p-n MOS device, a d-c bias voltage of about +0.2 volts is quiescently applied to the probe tip 27 of FIG. 4. Further, an a-c voltage at a frequency of approximately ten kiloHertz, and having a peak-to-peak value of about 0.1 volts, is superimposed on the d-c bias. Thus, a composite variable bias voltage, always positive in value, is applied to the probe tip. Additionally, the tip 27 is successively stepped from left-to-right in the indicated X direction at a step frequency of, for example, about 256 steps per second. For each micron of travel in the X direction, the probe tip is controlled to make 512 steps. At each step, as the applied positive bias voltage is varied, a measurement of dC/dV is taken.

For illustrative purposes, the probe tip 27 is shown in FIG. 4 positioned at five different spaced-apart locations overlying the particular n-p-n MOS device sample to be scanned. At its left-most position, the tip 27 overlies the n-type region 46.

Figure 5:
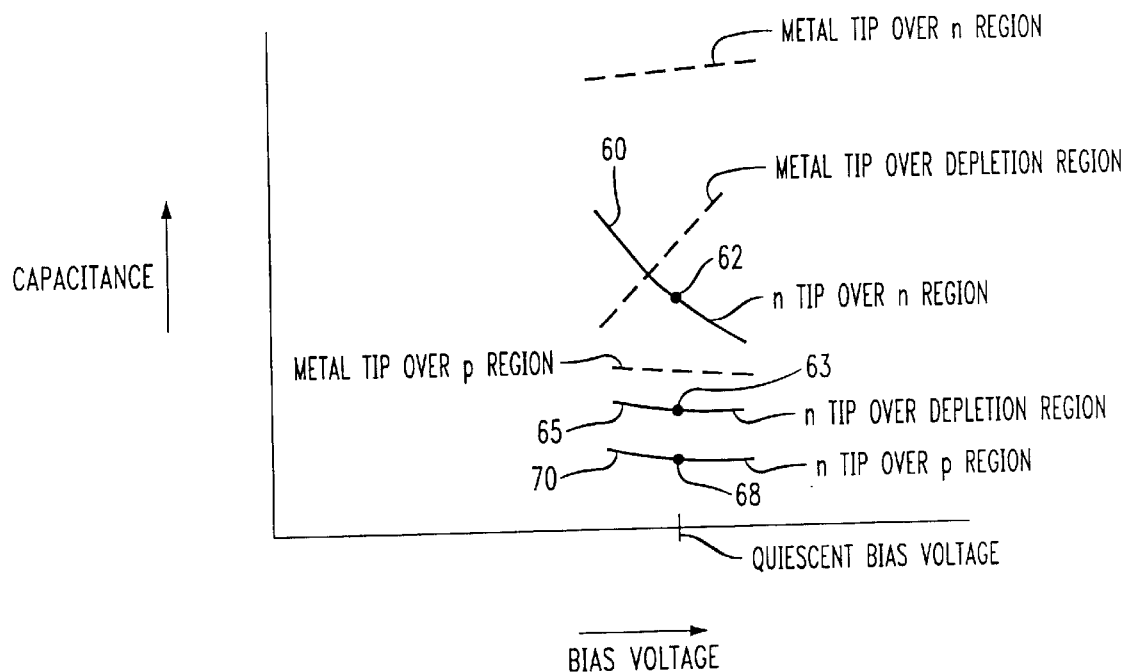
FIG. 5 is a plot of capacitance versus bias voltage, at various locations on a sample being probed, for a metal-coated tip and for a tip made in accordance with the present invention.

For the left-most probe position shown in FIG. 4, wherein the tip overlies the n-region 46, curve 60 of FIG. 5 indicates the manner in which the capacitance between the tip 27 and the conductive layer 42 varies with changes in the applied bias voltage. Illustratively, as specified above, the quiescent or d-c bias voltage is about +0.2 volts. This bias value is denoted on the curve 60 by point 62.

As the bias voltage applied to the tip 27 overlying the n-region 46 of FIG. 4 is varied (assume, for example, a positive increase in bias voltage), the additional vertically extending depletion that occurs in the laterally confined geometry of the small tip 27 tends to be relatively large. By contrast, only a relatively small additional vertically extending accumulation occurs in the laterally wide n-region 46. Thus, even if the concentrations in the tip 27 and in the region 46 are about the same, the decrease in capacitance attributable to the doped tip 27 predominates as the bias voltage goes more positive. And if, advantageously, the concentration of dopants in the tip is selected to be less than that in the n-region 46, even more of the positive change in bias voltage will appear across the tip, which will even further enhance depletion in the tip and cause an even greater decrease in the overall measured capacitance.

Thus, as specified above, a negative and appreciable change in capacitance occurs over the probed n-region 46 as the positive bias voltage applied to the doped tip 27 is made more positive. This is graphically represented by the steeply downwardly sloping curve 60 of FIG. 5. In the particular illustrative example specified herein, wherein an a-c signal having a peak-to-peak value of about 0.1 volts is superimposed on a positive d-c bias voltage of approximately +0.2 volts, the resulting overall dC/dV while the tip 27 overlies the n-region 46 of FIG. 4 is actually measured to be about −2 attofarads (af) per volt.

Figure 6:
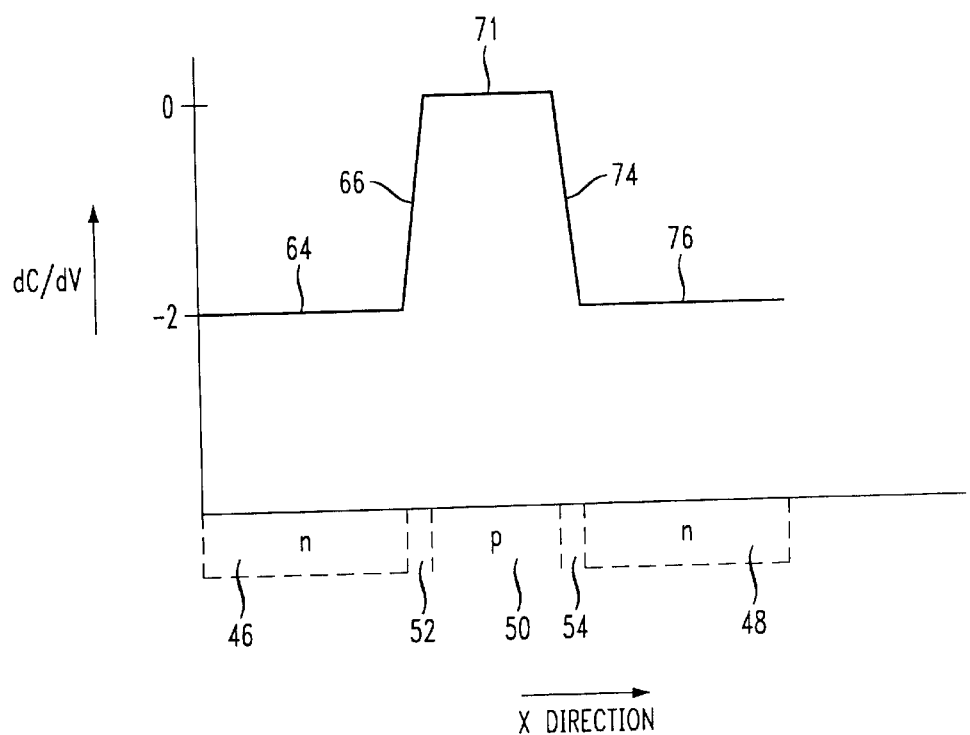
FIG. 6 is a graphical representation of dC/dV as the sample of FIG. 4 is probed, in accordance with the invention, at successive X-direction positions.

The aforementioned value of −2 af per volt is plotted in FIG. 6, where the indicated X direction corresponds to the X direction in FIG. 4. This measured value remains relatively constant for as long as the stepping probe tip overlies the n-region 46 of FIG. 4. This relatively constant horizontal portion of the FIG. 6 plot, designated by reference numeral 64, thus represents in effect the carrier profile of the scanned n-region 46.

Assume now that the scanning probe tip is positioned over the depletion region 52 shown in FIG. 4, as represented by the second-from-the-left tip 27. Some electrons exist in the depletion region 52, having been attracted there from the n-region 46 by the positively biased tip 27. But the concentration of carriers in the tip 27 considerably exceeds that in the depletion region 52. Further, because the concentration of electrons in the depletion region 52 is less than the concentration of electrons in the previously scanned n-region 46, the absolute value of the capacitance of the overall structure, as measued overlying the depletion region 52 at the quiescent bias voltage, is less than it was quiescently overlying the n-region 46. Point 63 on curve 65 of FIG. 5 indicates this lower capacitance value.

As the bias voltage is varied, with the tip 27 overlying the depletion region 52 (FIG. 4), most of the voltage change appears across the relatively lightly doped depletion region 52. But relatively little additional accumulation occurs in the region 52 because most of the electrons were already previously accumulated. And the additional accumulation that does occur does so diffusely over a laterally extending portion of the region 52. Thus, little increase occurs in the overall measured capacitance due to changes in the sample. Moreover, although the tip 27 depletes further to only a relatively small extent, that change is in a direction to cause a decrease in the overall measured capacitance. Therefore, the net change in the overall measured capacitance of the structure is detected as being extremely small as the bias voltage is varied. This is represented by the relative flatness of the curve 65 shown in FIG. 5.

Accordingly, shortly after the tip 27 steps from a position overlying the n-region 46 of FIG. 4 to a position overlying the depletion region 52, dC/dV is (for a d-c bias voltage of about 0.2 volts) in practice measured to have an extremely small value (approximately zero). And, since the p-n junction in the herein-considered device structure exists in fact very close to the boundary between the regions 46 and 52 of FIG. 4, the point at which the measured dC/dV changes from −2 af per volt to a value of about zero af per volt indicates with relatively good accuracy the actual physical location of the p-n junction in the structure. This transition in the measured value of dC/dV is indicated by nearly vertical segment 66 of the plot shown in FIG. 6.

Assume now that a doped semiconductor tip made in accordance with the invention is positioned over the p-type channel region 50 of the device structure shown in FIG. 4, as indicated by the third-from-the-left tip 27. In this case, the concentration of carriers in the tip 27 is considerably greater than the concentration of carriers in the underlying region 50 of the sample being probed. At the herein-specified quiescent positive bias voltage, the tip 27 and the region 50 are both depleted to some extent in the vicinity of the oxide layer 28. Hence, the absolute value of the capacitance at this tip position, at the quiescent bias voltage, is even smaller than it was when the tip was positioned over the depletion region 52. The value of this relatively small capacitance is indicated by point 68 on curve 70 in FIG. 5.

As the positive bias voltage is increased, with the tip 27 overlying the p-region 50, most of the voltage change appears across the relatively lightly doped sample. But, since at the indicated quiescent bias voltage, the region 50 is already substantially depleted, little additional depletion occurs therein. And whatever additional depletion occurs in the region 50 tends to be laterally distributed, thereby not substantially affecting the tip-to-sample capacitance. Also, the relatively small voltage change appearing across the tip 27 causes little additional depletion to occur therein. As a result, the overall change in the measured capacitance of the device structure at the indicated measurement position is exceedingly small as the applied bias voltage is varied. This is graphically represented by the flat curve 70 of FIG. 5.

Thus, at each position at which the tip 27 overlies the p-region 50, dC/dV is measured to be exceedingly small (for example, approximately zero). This is represented in FIG. 6 by the portion of horizontal segment 71 of the indicated plot that overlies the indicated p-region 50.

Subsequent stepping of the doped probe tip 27 of FIG. 4 over the depletion region 54 and the n-region 48 of the indicated sample produces dC/dV values that are represented in FIG. 6 by segments 74 and 76, respectively. The resulting overall plot of FIG. 6 is a faithful indication of the doping profile of the aforespecified n-p-n MOS device. Compared to images obtained in a conventional SCM system, the plot of FIG. 6 is characterized by better resolution, better contrast, more stable contrast and more accurate location of the p-n junctions in the scanned device.

As indicated earlier above, better resolution with a doped tip made in accordance with the present invention stems in part from the fact that such a tip has an extremely small size. But, significantly, the better resolution attainable with such a small doped tip also comes from the fact that the depletion effects that the inventive imaging process largely depends on are confined to the tip. By contrast, with a metal-coated tip in a conventional SCM system, depletion and accumulation effects occur only in the sample. With a metal-coated tip, these effects in the sample tend to be laterally diffuse. The lateral extent of these effects inevitably exceeds the physical dimensions of the tip. On the other hand, depletion effects in a small doped tip made in accordance with the present invention are physically confined to the small lateral dimensions of the tip. Thus, the size of the doped tip itself approximately determines the resolution of the herein-described scanning-depletion-microscopy process.

Also, in a conventional SCM system utilizing a metal-coated tip, scanning over a metallic region produces virtually no dC/dV as the bias voltage is varied. Similarly, with a metal-coated tip, scanning over an insulating region also produces virtually no dC/dV. In accordance with the invention, scanning over an insulating region with a doped tip would also produce virtually no dC/dV as the bias voltage is varied. (This result can be derived in effect from the case described above wherein the tip 27 was over the relatively lightly doped p-region 50 and the measured dC/dV value was determined to be approximately zero. In the limit, as the doping in the region 50 is reduced further, the region becomes more insulating-like in character.) But, when scanning an underlying metallic region, an imaging system including a doped tip made in accordance with the present invention would provide a relatively large dC/dV signal as the bias voltage is varied. This is directly attributable to significant depletion effects occurring in the physically confined doped tip. (This result can be derived from the case described above wherein the tip was over the relatively heavily doped n-region 46 and dC/dV had a relatively large value. In the limit, as the doping in the region 46 is increased further, the region can be considered to be metal-like.) Thus, an imaging system made in accordance with the principles of the present invention is also capable of providing contrasting images between metals and insulators.

As specified above, resolution is improved because depletion is confined to a tip with a small diameter. The small diameter of the tip makes it feasible to identify with high resolution the boundary between a heavily doped region and a built-in depletion layer. The high contrast develops from the changes induced by the depleting tip on the total capacitance. The optimum contrast is achieved by controlling the bias conditions. Specifically, the optimum contrast will depend on the thickness of the layer 28 (FIG. 2), the quality (trap density) of the layer 28, the detection efficiency and the flat-band voltage. (The doping type of the tip relative to the doping type of the sample will determine the flat-band voltage.) The optimum bias voltage is not necessarily positive or negative, but rather depends on all of these factors. In practice, the bias voltage is determined by the flat-band voltage, and the a-c signal level should be less than or equal to the d-c bias voltage. Enhancement of contrast in a probed sample, in accordance with the invention, is possible based on effective use of the bias voltage relative to the flat-band voltage and because of the particular manner in which the capacitances add.

In summary, in accordance with one specific illustrative embodiment of the principles of the present invention, a small doped semiconductor probe tip is utilized as an active dynamic sensing element for scanning-depletion-microscopy carrier profiling of semiconductor devices. By properly selecting the doping of the tip and the value of the bias applied thereto, accurate high-resolution and high-contrast images representative of the carriers in semiconducting, metallic and insulating regions of a probed device can be obtained.

Finally, it is to be understood that the above-described arrangements and techniques are only illustrative of the principles of the present invention. In accordance with these principles, numerous modifications and alternatives may be devised by those skilled in the art without departing from the spirit and scope of the invention. Thus, for example, although specific emphasis above was directed to probing an n-p-n MOS device with a positively biased n-doped tip, it is evident that images like those specified herein can be obtained by probing a p-n-p MOS device with a negatively biased p-doped tip. Also, by selectively changing the concentration and/or the quiescent bias point of the doped tip, the sensitivity of the technique can be controllably adjusted.

More generally, it is to be understood that the principles of the invention encompass any tip made of a material capable of being depleted. For example, consider a metal with a depletion length of the order of 0.5 nm. If the tip diameter is one nm, such a metal tip will provide the same flexibility that depleting semiconductor tips do, but with potentially higher resolution since the tip diameter is necessarily smaller. Further, consider a semi-metal such as bismuth or graphite which have depletion lengths of the order of four nm. In those cases, a tip diameter less than ten nm would be useful to provide an active probe. In summary, if the depletion length of the tip material is comparable to or less than the tip diameter, such a tip is a candidate for use as an active probe. And, with semiconductor tips, different doping levels and different doping types, as well as different doping profiles (imposed, for example, by different tip geometries) can be utilized to advantage to be sensitive to a particular carrier density or to enhance contrast and/or resolution. The concentration of carriers in the tip can be varied to select the carrier density contour of interest in the sample. In this way, the tip characteristic can in effect be tailored to a particular sample.

Further, although specific emphasis above was directed to imaging particular semiconductor samples (n-p-n or p-n-p transistors) or metals or insulators, the invention is also applicable to imaging a wide variety of structures. Thus, for example, semiconductor structures of different doping types and varying concentrations (for instance, $n^+/n^-/i$) can be effectively imaged. Additionally, combinations of doped semiconductor/metal/insulator and other materials (such as superconductors) can also be imaged by utilizing the inventive techniques described herein.

What is claimed is:

1. An imaging system comprising
means for holding a sample to be probed, said sample comprising one or more semiconducting portions each characterized by a specified carrier concentration that imparts to each respective portion only a semiconducting electrical property,
an active tip capable of exhibiting depletion effects and adapted to successively probe spaced-apart portions of said sample while in contact therewith, said tip comprising a semiconductor material having a semiconducting electrical property and being doped to exhibit a specified carrier concentration on the order of or less than the highest concentration of carriers in any semiconducting sample portion to be probed, the concentration of carriers in said tip being such as to maintain a semiconducting electrical property in said doped tip,
means for applying a variable bias voltage of a specified polarity between said tip and said holding means to vary the voltage applied to said sample at each probed portion and to cause carriers to be depleted in said semiconducting tip away from the contact between said tip and the probed sample portion,
means for positioning said tip overlying successive portions of said sample,
and means for measuring the change in capacitance at each probed portion as the voltage applied thereto is varied.

2. A system as in claim 1 wherein said tip comprises a doped semiconductor material.

3. A system as in claim 2 wherein said sample to be probed comprises a semiconductor device structure.

4. A system as in claim 3 wherein said sample is a semiconductor device structure that includes at least one n-doped portion and at least one p-doped portion, said portions having respectively different carrier concentrations, and wherein said tip is (a) doped with the same type dopant as the more heavily doped of said n- and p-doped portions and (b) has a carrier concentration that is on the order of or less than that of said more heavily doped portion.

5. A system as in claim 4 wherein said sample comprises an n-p-n MOS device, and wherein said tip is n-doped and positively biased.

6. A system as in claim 5 wherein the concentration of n-type carriers in said n-portions is greater than the concentration of carriers in said p-portion, and wherein the concentration of n-type carriers in said tip is on the order of or less than the concentration of carriers in said n-portions.

7. A system as in claim 4 wherein said sample comprises a p-n-p device, and wherein said tip is p-doped and negatively biased.

8. A system as in claim 7 wherein the concentration of p-type carriers in said p-portions is greater than the concentration of carriers in said n-portion, and wherein the concentration of carriers in said tip is less than the concentration of carriers in said p-regions.

9. Apparatus for imaging the carrier profile of regions in a sample, said sample comprising one or more doped semiconducting regions each characterized by a specified carrier concentration that imparts to each respective region only a semiconducting electrical property, said apparatus comprising an active tip capable of exhibiting depletion effects and adapted to successively probe the semiconducting regions of said sample, said tip comprising a doped semiconductor material having a semiconducting electrical property, said tip having a specified carrier concentration on the order of or less than the highest concentration of carriers in any semiconducting sample region to be probed, the concentration of carriers in said tip being such as to maintain in said doped tip a semiconducting electrical property, means for biasing said tip with respect to said sample, means for successively probing specified portions of the respective regions of said sample with said tip while varying the voltage provided by said biasing means and thereby depleting carriers from said tip, and means for measuring the change in capacitance between the tip and said sample as the bias voltage is varied.

10. Apparatus as in claim 9 wherein the depletion-length characteristic of the material of said tip is comparable to or less than the diameter of said tip.

11. Apparatus as in claim 10 wherein said tip comprises n-doped semiconductor material and is positively biased.

12. Apparatus as in claim 11 wherein said sample to be imaged is an n-p-n MOS device.

13. Apparatus as in claim 10 wherein said tip comprises p-doped semiconductor material and is negatively biased.

14. Apparatus as in claim 13 wherein said sample to be imaged is a p-n-p MOS device.

15. A method for imaging the carrier profile of a device structure that includes doped n- and p-type semiconducting regions having respectively different carrier concentrations each of which imparts to said doped region only a semiconducting electrical property, said method comprising the steps of successively probing said regions with a probe tip having a semiconducting electrical property, wherein said semiconducting tip is of the same conductivity type as the sample region having the higher carrier concentration and is characterized by a carrier concentration that is on the order of or less than that of the semiconducting sample region with the higher concentration, while succesively probing the regions of said sample, biasing said tip with respect to each semiconducting region of said sample to attract carriers in the tip away from the interface between the tip and sample, thereby depleting carriers in said tip, and measuring the change in capacitance between the tip and sample at each successively probed region.

16. A method as in claim 15 wherein said device structure comprises an MOS device and said semiconducting regions include spaced-apart source and drain regions of one conductivity type formed in a substrate of the opposite conductivity type.

\* \* \* \* \*